United States Patent
Graffigna et al.

(10) Patent No.: US 12,150,757 B2
(45) Date of Patent: Nov. 26, 2024

(54) APPARATUS AND METHOD FOR MEASURING CLINICAL-AUDIOMETRIC PARAMETERS

(71) Applicant: Neuranix S.R.L., Naples (IT)

(72) Inventors: Carlos Esteban Graffigna, La Rioja (AR); Domenico Stanzial, Rome (IT)

(73) Assignee: Neuranix S.R.L., Naples (IT)

(*) Notice: Subject to any disclaimer, the term of this patent is extended or adjusted under 35 U.S.C. 154(b) by 0 days.

(21) Appl. No.: 18/017,990

(22) PCT Filed: Oct. 21, 2021

(86) PCT No.: PCT/IB2021/059732
§ 371 (c)(1),
(2) Date: Jan. 25, 2023

(87) PCT Pub. No.: WO2022/084922
PCT Pub. Date: Apr. 28, 2022

(65) Prior Publication Data
US 2023/0284935 A1    Sep. 14, 2023

(30) Foreign Application Priority Data
Oct. 21, 2020   (IT) .................. 102020000024856

(51) Int. Cl.
| | | |
|---|---|---|
| A61B 5/12 | (2006.01) | |
| A61B 5/00 | (2006.01) | |
| G16H 40/63 | (2018.01) | |
| G16H 50/30 | (2018.01) | |

(52) U.S. Cl.
CPC ............ *A61B 5/126* (2013.01); *A61B 5/6817* (2013.01); *A61B 5/7257* (2013.01); *G16H 40/63* (2018.01); *G16H 50/30* (2018.01); *A61B 2560/0223* (2013.01); *A61B 2560/0443* (2013.01); *A61B 2562/0204* (2013.01); *A61B 2562/04* (2013.01)

(58) Field of Classification Search
None
See application file for complete search history.

(56) References Cited

U.S. PATENT DOCUMENTS

| | | |
|---|---|---|
| 5,792,073 A | 8/1998 | Keefe |
| 2008/0194984 A1* | 8/2008 | Keefe ................. A61B 5/121 73/585 |

FOREIGN PATENT DOCUMENTS

| | | |
|---|---|---|
| EP | 2 800 514 A1 | 11/2014 |
| EP | 2800514 B1 | 4/2021 |

(Continued)

OTHER PUBLICATIONS

K.M. Nørgaard et al., "Reproducing Ear-Canal Reflectance Using Two Measurement Techniques in Adult Ears." The Journal of the Acoustical Society of America, vol. 147, No. 4, pp. 2334-2344, 2020.

(Continued)

*Primary Examiner* — Tse W Chen
*Assistant Examiner* — Michael A Catina
(74) *Attorney, Agent, or Firm* — Quarles & Brady LLP (57) ABSTRACT

Apparatus and method for determining the immiittance of a middle ear for clinical-audiometric investigations in a wide range of frequencies at ambient pressure, based on MEMS microphone technology and on measuring the acoustic pressure wave and the corresponding acoustic velocity wave by means of a pressure-pressure probe.

22 Claims, 2 Drawing Sheets

(56) References Cited

FOREIGN PATENT DOCUMENTS

WO    WO 2013/102867      7/2013
WO    WO 2018/146609 A1   8/2018

OTHER PUBLICATIONS

D. Ćirić et al., "Acoustic Impedances of Audiometric Earphones Coupled to Different Loads." Forum Acusticum, pp. 215-220, Budapest 2005.
H. Hudde, "Measurement of the Eardrum Impedance of Human Ears." The Journal of the Acoustical Society of America, vol. 73, No. 1, pp. 242-247, 1983.
D. Stanzial et al., "Protocollo di Calibrazione in Ampiezza e Fase Per Sonde Pressione-Velocità in un Campo di Riferimento a Onde Piane Progressive." Associazione Italiana di Acustica. 2017.
D. Stanzial et al., "Funzione di Calibrazione in Ampiezza e Fase per Sonde Pressione-Velocità Ottenuta in Campi di Riferimento Reattivi." Associazione Italiana di Acustica, 2018.
D. Stanzial et al., "Protocollo di Calibrazione in Ampiezza e Fase per Sonde Pressione-Velocità in un Campo di Riferimento a Onde Piane Progressive." Associazione Italiana di Acustica. 2017. English Language Translation is also enclosed.
D. Stanzial et al., "Funzione di Calibrazione in Ampiezza e Fase per Sonde Pressione-Velocità Ottenuta in Campi di Riferimento Reattivi." Associazione Italiana di Acustica, 2018. English Language Translation is also enclosed.

\* cited by examiner

APPARATUS AND METHOD FOR MEASURING CLINICAL-AUDIOMETRIC PARAMETERS

CROSS-REFERENCE TO RELATED APPLICATIONS

This application is a national stage application of PCT/IB2021/059732, filed on Oct. 21, 2021, which claims priority to Italian Application Serial No. 102020000024856, filed Oct. 21, 2020, each of which are hereby incorporated herein by reference in their entirety.

The present invention relates to an apparatus and method for determining the immittance of a middle ear for clinical-audiometric investigation in a in a simple, non-invasive, reliable and economical way.

Such invention is based on MEMS microphone technology and on the simultaneous measurement of the acoustic pressure wave and the corresponding acoustic velocity wave with pressure-pressure probe.

The present invention is mainly oriented to ear impedancemetry, also called tympanometry, towards diagnostic applications for determining the state of the tympanic membrane of a middle ear in humans or in another animal equipped with an ossicular tympanic system and external auditory canal, such as for example a dog or a cat.

Classical tympanometry allows to carry out an objective analysis of the functional state of the external and middle ear in order to diagnose the main pathologies. It consists in sending a mono-frequency sound wave, usually around 226, 678, 800 and 1000 Hz and evaluating the variations in the acoustic volumetric impedance, measured at the tympanic membrane level, as a function of pressure variations artificially created in the external auditory canal, usually included in a range between −600 and +400 daPa.

The classical tympanometric technique has disadvantages. In fact, a classic tympanometric test is carried out with indirect measurements, using monofrequency stimuli, and with an invasive method, due to an outside induced variation of the static pressure in the auditory canal, which is particularly annoying especially for infants and children.

As an alternative to the classical tympanometric technique, a broadband tympanometric technique with p-v microprobes has also been developed, which detects the dependence of the specific admittance of the system including the canal and the eardrum on the frequency of a sound wave which can vary from 50 Hz to 8 kHz, at constant static pressure. This technique is based on microprobes p-v (pressure-velocity) with MEMS technology (Micro Electro-Mechanical Systems) capable of directly measuring the values of pressure and velocity in response to an external stimulus.

However, this technique also has disadvantages in that p-v microprobes have high costs and, moreover, the velocity probe is fragile and easily subject to breakage.

The object of the present invention is overcoming the described disadvantages, allowing to carry out clinical-audiometric investigations on the functional state of an ear in a reliable, non-invasive, and economical way.

The measurement uncertainty of the ear canal reflectance associated with the conventional measurement technique was investigated by reproducing ear canal reflectance measurements using two different measurement techniques, as reported in Kren Monrad Nrgaard et al.: "Reproducing ear-canal reflectance using two measurement techniques in adult ears", *The Journal Of The Acoustical Society Of America*, American Institute Of Physics For The Acoustical Society Of America, New York, NY, US, vol. 147, no. 4, 17 Apr. 2020 (2020-04-17), pages 2334-2344, XP012246238, ISSN:0001-4966, DOI: 10.1121/10.0001094.

It is specific subject matter of the present invention a method for determining the admittance of an auditory canal for clinical-audiometric investigations, the method comprising at least one or more iterations of a procedure, in which each iteration is associated with a respective coupling configuration (Q, Q1, Q2) between an impedance probe and the auditory canal, in which said procedure includes the following steps:

A. coupling the calibrated sealed impedance probe having a known air volume $V_{probe}$, through a first end thereof, with the auditory canal so that:

the air volume $V_{probe}$ sealed inside the impedance probe and the air volume $V_{canal}$ inside the auditory canal form an overall air volume $V_{overall}$, and a longitudinal axis of the impedance probe is substantially coincident to a longitudinal axis of the auditory canal;

B. sending a broadband exciting sound signal s(t) to the auditory canal through a speaker of the impedance probe, such speaker being located at a second end of the impedance probe opposed to the first end;

C. directly detecting an acoustic pressure $p_1(t)$, $p_2(t)$ back from the auditory canal in at least two points $x_1$ and $x_2$, respectively, located along the longitudinal axis of the impedance probe at distance $\Delta x_{12}$ between them, by means of a microphone array that is included in the impendence probe and outputs electric signals $r_1(t)$ and $r_2(t)$;

D. acquiring and discretizing the output electric signals $r_1(t)$ and $r_2(t)$ from the microphone array, obtaining discretized signals $r_1(n)$ and $r_2(n)$ respectively, with $n \in [1; N]$, $N \in \mathbb{N}$;

E. calculating a first impulse response $\delta_1^{au}(n)$ and a second impulse response $\delta_2^{au}(n)$ by the following equations:

$$\delta_1^{au}(n) = IFFT\left\{\frac{FFT\{s'(t)\}}{FFT\{r_1(t)\}}\right\}$$

$$\delta_2^{au}(n) = IFFT\left\{\frac{FFT\{s'(t)\}}{FFT\{r_2(t)\}}\right\}$$

where s'(t) is the time reversed broadband sound signal s(t), FFT is a Fast Fourier Transform and IFFT is an inverse FFT;

F. calculating an impulse response $\delta_p^{au}(n)$ of the acoustic pressures $p_1(t)$ and $p_2(t)$ and an impulse response $\delta_v^{au}(n)$ of velocity of an air particle at measurement point $x_0$ along the longitudinal axis of the impedance probe:

$$\delta_v^{au}(n) = \frac{\delta_1^{au}(n) - \delta_2^{au}(n)}{(\rho \cdot \Delta x_{12})} + \delta_v^{au}(n-1)$$

$$\delta_p^{au}(n) = \frac{\delta_1^{au}(n) + \delta_2^{au}(n)}{2}$$

such a measurement point $x_0$ being a centre point between points $x_1$ and $x_2$;

G. converting the impulse responses $\delta_p^{au}(n)$ $\delta_v^{au}(n)$ of pressure and velocity to pressure and velocity physical units by multiplying each one by a calibration constant α and β known a priori, respectively, as follows:

$\delta_p(n)[\text{Pascal}] = \alpha \cdot \delta_p^{au}(n)$ $\delta_v(n)[\text{Pascal meter/second}] = \beta \cdot \delta_v^{au}(n)$ H. calculating (270) frequency spectra $\hat{P}^*(\omega_m)$, $\hat{V}^*(\omega_m)$ of the impulse responses of pressure and velocity respectively, through Fast Fourier Transform, as follows:

$$\begin{cases} \hat{V}^*(\omega_m) = FFT\{\delta_v(n)\} \\ \hat{P}^*(\omega_m) = FFT\{\delta_p(n)\} \end{cases}$$

where $\omega_m$ is a discretized frequency with $m \in [1; N/2]$;

I. calculating an admittance $\hat{Y}^*(\omega_m)$ as a ratio between a cross spectrum $\hat{G}_{pv}(\omega_m)$ of the spectrum of the acoustic pressure impulse response and of the spectrum of the acoustic velocity impulse response, and an auto spectrum $\hat{G}_{pp}(\omega_m)$ of the spectrum of the acoustic pressure impulse response:

$$\hat{Y}^*(\omega_m) = \frac{\hat{G}_{pv}(\omega_m)}{\hat{G}_{pp}(\omega_m)} = \frac{\hat{V}^*(\omega_m) \cdot \hat{P}^*(\omega_m)}{\hat{P}^*(\omega_m) \cdot \hat{P}^*(\omega_m)}$$

L. obtaining a calibrated frequency spectrum $\hat{Y}(\omega_m)$ of the admittance through a calibration function $\Gamma(\omega_m)$ known a priori, according to the equation:

$\hat{Y}(\omega_m) = \Gamma(\omega_m) \cdot \hat{Y}^*(\omega_m)$ said steps D to L being performed by a control and processing device.

According to another aspect of the invention, said calibration constant α and β, and the calibration function $\Gamma((\omega_m)$ can be known a priori, optionally provided by manufacturer of microphones.

According to a further aspect of the invention, said exciting sound signal s(t) can be a sweep signal, optionally a linear or logarithmic sinusoidal signal, varying from a minimum frequency $F_{min}$ greater than 100 Hz to a maximum frequency $F_{max}$ less then 5000 Hz over a time $T_{sweep}$ less than 10 seconds, optionally equal to 2 seconds, more optionally equal to 1 second.

According to an additional aspect of the invention, said distance $\Delta x_{12}$ can be equal to 12 mm.

According to another aspect of the invention, said step B can comprise the substeps:
B.1 synthesizing a digital sweep signal s(n) by a signal generator,
B.2 converting the digital sweep signal s(n) into a broadband exciting sound signal s(t) to be input to the speaker through a D/A converter.

According to a further aspect of the invention, said step D can be implemented through an A/D converter synchronized with the D/A converter.

According to an additional aspect of the invention, said calibrated frequency spectrum $\hat{Y}(\omega_m)$ of the admittance can be further input to a display to be displayed.

According to another aspect of the invention, said impedance probe and said auditory canal can be coupled into a first coupling configuration (Q1), said exciting sound signal s(t) can be a fast sweep signal $s^{fast}(t)$ varying in frequency over a time $T_{sweep}^{fast}$ less than one second, to obtain a first calibrated admittance $\hat{Y}_1(\omega_m)$, and said procedure can comprise further the additional step:

M. checking whether a resonance condition in the calibrated admittance $\hat{Y}_1(\omega_m)$ is satisfied, thereby a peak of the module of the first calibrated admittance $\hat{Y}_1(\omega_m)$ corresponds to zero-crossing of its phase, and wherein:
if a resonance condition does not occur, another iteration of said procedure comprising steps A to M is implemented, wherein the impedance probe and the auditory canal are coupled in another coupling configuration (Q2) that is different from the previous coupling configuration (Q1) and the exciting sound signal s(t) is the fast sweep signal $s^{fast}(t)$;
if a resonance condition occurs, steps B to L of such procedure are implemented, wherein the coupling configuration is the one for which the resonance condition occurs and the exciting sound signal s(t) is a sweep signal varying in frequency over a time greater than the time $T_{sweep}^{fast}$ of the fast sweep signal $s^{fast}(t)$, and said one or more iterations of said procedure end.

It is another specific subject matter of the present invention a clinical-audiometric investigation method comprising the method for determining the admittance of an auditory canal according to this invention, wherein the investigation is implemented in the coupling configuration (Q, Q1, Q2) of the last one or more iterations and wherein the exciting sound signal s(t) varies in frequency over a time grater or equal to 1 second.

It is an addition specific subject matter of the present invention an apparatus for implementing the method for determining the admittance of an auditory canal according to any one of claims 1 to 7, that includes:
an impedance probe configured to be coupled with an auditory canal (6) having
a box-like body with a first end configured to be coupled to the auditory canal,
a speaker located close to a second end of the box-like body, that is opposed to the first end, configured to emit an exciting sound signal, the box-like body being sealed and containing inside an air volume $V_{probe}$ at atmospheric pressure,
a microphone array housed inside the box-like body and configured to detect signals back from the auditory canal, comprising at least a first microphone and at least a second microphone placed between them at a distance $\Delta x_{12}$ that depends on the frequencies of the exciting sound signal s(t), each microphone being configured to directly detect a return sound pressure p(x, t) as a function of time t and to output an electrical signal r (x, t);
a control and processing device configured to control and process input and output signals of the impedance probe and to implement step B to L, having:
a generation unit configured to generate a digital signal s(n) and send it to the speaker through a D/A conversion board that is removably coupled to the speaker, and
an acquisition sound board configured to acquiring output signal from microphone array, through an A/D conversion board that is removably coupled to the microphone array (8),
the impedance probe and the control and processing device being removably coupled among them.

According to another aspect of the invention, said control and processing device can be further configured to implement said step M.

According to a further aspect of the invention, said box-like body can be hollow cylindrical shaped.

According to an additional aspect of the invention, said apparatus can be configured to input broadband exciting sound signal s(t) in a frequency range between 100 Hz to 5000 Hz and wherein the distance $\Delta x_{12}$ is equal to 12 mm.

According to another aspect of the invention, said second end is provided with an adapter configured to get easy coupling with the auditory canal, optionally said adapter being removable.

According to a further aspect of the invention, said adapter is truncated cone shaped, optionally made of rubber latex.

The advantages offered by the method according to the invention are numerous and significant with respect to the solutions of the prior art.

The method of the present invention is not invasive because it allows to measure the acoustic admittance of the ear entry at ambient pressure without altering the static pressure of the patient's auditory canal. Another advantage is that of allowing the analysis of the functional state of the ear over a wide range of frequencies. In addition, the use of the p-p (pressure-pressure) technique to measure the acoustic admittance of the ear allows the use of pressure probes, i.e. microphones, based on MEMS technology, thus lowering the production costs of impedance probes.

For measuring the acoustic admittance, which is the reciprocal of the acoustic impedance, in the auditory canal it is necessary to measure the pressure and velocity signals obtained as a response to a sound stimulus sent at its entry. The p-p technique is based on the Euler acoustic wave equation which allows to reconstruct the velocity signal of an acoustic particle by numerically integrating the gradient signal of the acoustic pressure over time. This choice, in many ways not optimal from a metrological point of view, was however satisfactory in the frequency range required by the application, and currently offers a significant reduction in the production costs of the probe, thanks to the commercial success of the MEMS technologies applied to pressure microphones.

The present invention will be now described, by way of illustration and not by way of limitation, according to its preferred embodiments, by particularly referring to the Figures of the annexed drawings, in which.

Due to the conformation of the auditory canal, the air is constrained to oscillate substantially along the longitudinal axis of the auditory canal, therefore it is possible to approximate the velocity vector with the velocity along the direction of said axis, which we set as the x direction, or x axis.

Figure 1:
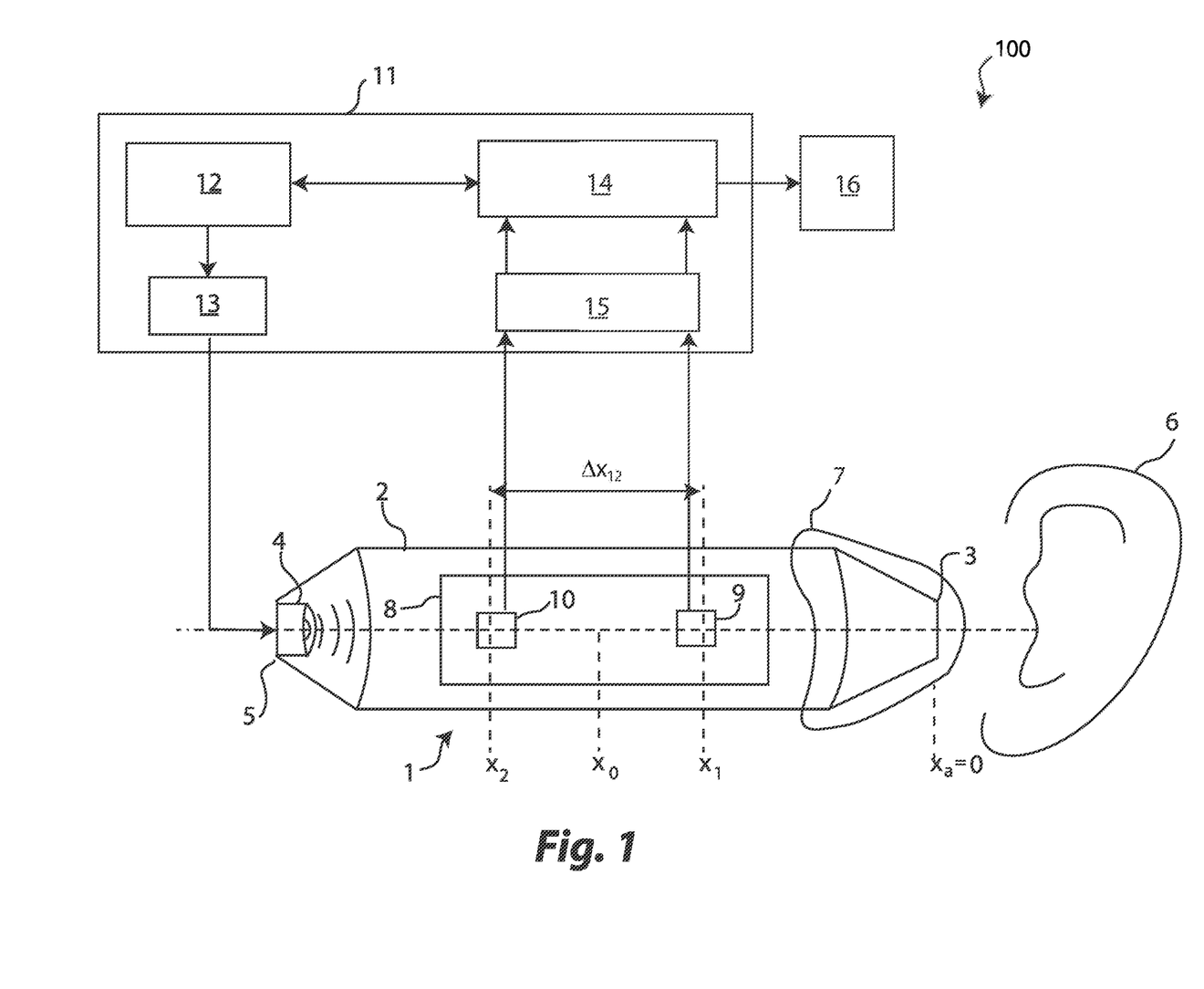
FIG. 1 is a schematic block diagram of preferred embodiment of the apparatus for measuring the acoustic admittance of an ear according to the invention.

With reference to FIG. 1, an apparatus 100 comprises an impedance probe 1 having a box-like body 2 with a first end 3 configured to be coupled with an external measurement environment, which in the case shown in FIG. 1 is an external auditory canal 6 of a patient. The box-like body 2 contains within it at least one speaker 4 placed in proximity to a second end 5 thereof, opposite the first end 3.

The speaker 4 is configured to emit an acoustic signal s(t) for input to the external auditory canal 6.

The box-like body 2 of the preferred embodiment of FIG. 1 has a hollow cylindrical shape. Conventionally, we set the position along the x axis of the first end 3, $x_a$, as the origin of the x axis, $x_a=0$.

The box-like body 2 is rigid, optionally made of brass or rigid resin. The box-like body 2 is sealed and contains within it a known air volume $V_{probe}$ at atmospheric pressure. The coupling of the impedance probe 1, through its first end 3, with the external auditory canal of a patient is such that the air volume $V_{probe}$ and an air volume $V_{canal}$ inside the auditory canal form an overall air volume $V_{overall}$ at atmospheric pressure, i.e. $V_{overall}=V_{probe}+V_{canal}$. In other words, an overall volume $V_{overall}$ containing air at atmospheric pressure is bounded by the impedance probe and the auditory canal when they are coupled together.

Furthermore, the coupling is such that the axis passing between the geometric centres of the first end 3 and of the second end 5, conventionally the longitudinal axis of the impedance probe, is parallel, substantially coincident, with the axis of the auditory canal, that is the x axis.

In the preferred embodiment, the first end 3 is provided with an adapter 7, optionally having a truncated cone shape and made of rubber latex, configured to facilitate coupling to the external auditory canal 6. The adapter 7 can be removable to be replaced or cleaned before use on different patients.

A microphone array 8, that is configured to detect return signals from the external auditory canal 6, is housed in the box-like body 2. The microphone array 8 comprises a first microphone 9 and at least one second microphone 10, each one configured to directly detect a return acoustic pressure p(x, t) as a function of time t and provide with an electrical signal r(x, t), at a first measurement point $x_1$ and at a second measurement point $x_2$ respectively.

The distance $\Delta x_{12}$ between the first measurement point $x_1$ of the first microphone 9 and the second measurement point $x_2$ of the second microphone 10 depends on the frequency of the signal of interest. Ideally, for reconstructing the velocity signal from the pressure signals measured by two microphones, a different distance $\Delta x$ should be used for each frequency, that is for each wavelength, of the sound field to be measured.

In the preferred embodiment, an optimum distance is used to cover a range of working frequencies. To reduce the experimental error in the reconstruction of the velocity signal due to an error of the finite difference approximation at high frequencies, the measured wavelength must be greater than about six times the distance between the two microphones. For example, for a distance between probes equal to 50 mm, the high frequency limit of the sound field beyond which the experimental error significantly increases is 1.25 kHz, for a distance equal to 12 mm the high frequency limit is 5 kHz, and for a distance of 6 mm the high frequency limit is 10 kHz.

In the case of impedance measurement within an auditory canal of a human ear, the distance $\Delta x_{12}$ is equal to 12 millimeters to optimize the measurement of acoustic admittance in the 100-5000 Hz frequency range.

In other embodiments of the present invention, the microphone array 8 comprises a plurality of microphones greater than two, placed at different distances $\Delta x_{ij}$ from each other, so as to obtain a more accurate reconstruction of the velocity signal for each range of frequencies.

The minimum distance on the longitudinal axis between the second end 5 and the central point $x_0$ of the microphone array 8, i.e. between the first and second measurement points $x_1$, $x_2$, must be such as to minimize the microphone array 8 measurement error due to the proximity to a sound source. In the preferred embodiment, this distance is equal to 35 millimeters.

The impedance probe 1 is removably coupled with a control and processing device 11 configured to control and process the input and output signals from the impedance probe 1. The control and processing device 11 includes a generation unit 12 configured to generate a digital signal s(n) and send it to the speaker 4, through a D/A conversion board 13 which is removably connected to the speaker 4, and an acquisition sound board 14 configured to acquire the output signals from the microphone array 8, by means of an A/D conversion board 15, which is removably connected to the microphone array 8. The generation unit 12 and the acquisition sound board 14 are connected to each other. Optionally, the control and processing device 11 can be removably connected to one or more devices, such as for example PCs, smartphones and tablets, and/or to one or more screens 16 configured to display the signals controlled and processed by the control and processing device 11.

For the measurement of the acoustic admittance inside the auditory canal it is necessary to measure the acoustic pressure and particle velocity signals in the air obtained as a response to a sound stimulus sent at its entry, that is to the input signal. The impedance probe 1, as described in FIG. 1, allows to indirectly measure the velocity signal, starting from two acoustic pressure signals detected at a distance $\Delta x$ one from the other along the axis of the probe itself.

In fact, by considering a one-dimensional sound field in a medium with density p, then the Euler acoustic equation that links acoustic pressure p(x,t) and particle velocity v(x,t) to a point in the sound field can be written as:

$$\frac{\partial v(x,t)}{\partial t} = -\frac{1}{\rho}\frac{\partial p(x,t)}{\partial x} \qquad \text{(Eq. 1)}$$

from which one can get the velocity signal by integrating:

$$v(x,t) = -\frac{1}{\rho}\int_{-\infty}^{t}\frac{\partial p(x,t)}{\partial x}dt \qquad \text{(Eq. 2)}$$

By using the finite difference approximation method, the pressure gradient $$\frac{\partial p}{\partial x}$$

can be estimated in practice by measuring the pressures at two closely spaced points A and B separated by a distance $\Delta x$:

$$\frac{\partial p(x,t)}{\partial x} \approx \frac{p(B)-p(A)}{\Delta x} \qquad \text{(Eq. 3)}$$

Note that this approximation is valis only if $\Delta x$ is small compared with the shortest wave lengths in the measured sound field.

Substituting equation 3 into eq. 2, the velocity is calculated as:

$$v(x,t) = -\frac{1}{\rho\Delta x}\int_{-\infty}^{t} p(B)-p(A)\,dt \qquad \text{(Eq. 4)}$$

Similarly, the acoustic pressure can be estimated as the average of the pressures p(A) e p(B).

Therefore, for the impedance probe 1 it is possible it is possible approximating the spatial derivative of the pressure with its incremental ratio $\Delta x_{12}$ and performing integration over time to obtain the component of the velocity signal oriented along x direction:

$$v(x,t) \approx -\frac{1}{\rho\Delta x}\left[\int_{-\infty}^{t} p_1(x_1,\tau)-p_2(x_2,\tau)\,d\tau\right] \qquad \text{(Eq. 5)}$$

And calculating the pressure as $$p(x,t) = \frac{p_1(x_1,t)+p_2(x_2,t)}{2} \qquad \text{(Eq. 6)}$$

with $$p_1(x_1,t) = p\left(x_0+\frac{\Delta x}{2},t\right) e\ p_2(x_2,t) = p\left(x_0-\frac{\Delta x}{2},t\right) \qquad \text{(Eq. 7)}$$

where $p_1(x_1, t)$ e $p_2(x_2, t)$ are pressure signals measured through the first and the second microphone 9,10.

It is usual to refer the pressure and velocity signals, calculated through the equations 5 to 7, to the central point $x_0$ between the two microphones, which is therefore the actual measuring point $\{p(x_0, t); v(x_0, t)\}$.

To identify a linear time-invariant acoustic system, such as the auditory canal of a human or mammalian ear, it is necessary to know its transfer function by which it is possible to analyse its response to sound waves of any frequency. However, the study of impedance requires knowledge of the two acoustic pressure and velocity responses in the frequency domain. Thus, the most suitable stimulus to measure these responses must be able to excite the system in the whole range of frequencies that one plans to analyse, therefore this stimulus has to be generated by a signal whose average temporal energy is the same for each frequency component. For this reason, the calculation of the admittance is based on the impulse responses of the linear time-invariant acoustic system calculated from the measurements of the field excited with chirp or sweep signal, that is a frequency modulated signal wherein the instantaneous frequency varies linearly with time:

$$\delta(t) = IFFT\left\{\frac{FFT\{s'(t)\}}{FFT\{r(t)\}}\right\} \qquad \text{(Eq. 8)}$$

where $\delta(t)$ is the impulse response, IFFT is the Inverse Fast Fourier Transform, FFT(s'(t)) is the Fast Fourier Transform of the time-reversed sweep signal and FFT (r(t)) is the Fast Fourier Transform of the signal measured as the response of the system to the sweep signal stimulus.

Figure 2:
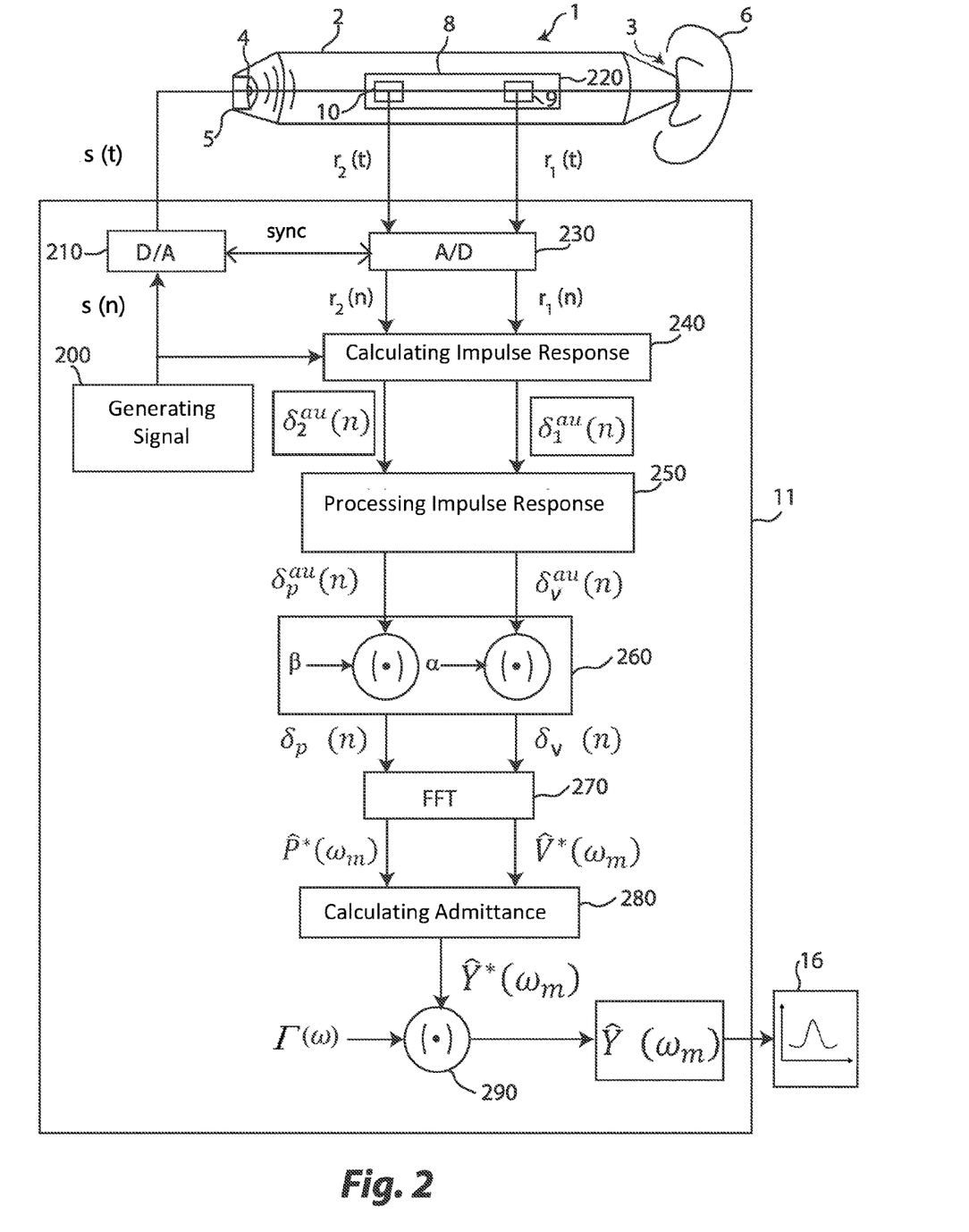
FIG. 2 shows a flow chart of the algorithm executed by a first preferred embodiment of the method for measuring the acoustic admittance of an ear according to the invention; In the Figures, identical reference numerals will be used for alike elements.

The flow chart of a preferred embodiment of the method for measuring the acoustic admittance of an ear is shown in FIG. 2 inside the block corresponding to the control and processing device 11 of the apparatus 100 of FIG. 1;

Preliminarily, the impedance probe 1 is calibrated, for example with a standard calibration method used in tympanometry to calculate the air volume $V_{probe}$ contained within impedance probe 1. For example, a classic method is the one known to those skilled in the art which uses three known volumes of air of 0.2 cc, 2 cc and 4 cc.

In an initial step, the calibrated impedance probe 1 is coupled to an auditory canal 6 through a first end (3) thereof in a coupling configuration (Q) such that its air volume $V_{probe}$ and an air volume $V_{canal}$ inside the auditory canal form an overall air volume $V_{overall}$, that is $V_{overall} = V_{probe} + V_{canal}$, and that its longitudinal axis is parallel, substantially coincident, with the axis of the auditory canal, that is the x axis.

Coupling configuration means the mutual and contact placement of the impedance probe 1 and auditory canal 6.

In step 200, the generation unit 12 generates, in other terms synthesizes, an excitation chirp or sweep signal s(n) which varies in frequency from a minimum frequency $F_{min}$ greater than 100 Hz to a maximum frequency $F_{max}$ less than 5000 Hz, in a time $T_{sweep}$ which is less than 10 seconds, optionally equal to 2 seconds, even more optionally equal to 1 second. In the preferred embodiment, the excitation sweep signal s (n) is a logarithmic or linear sinusoidal sweep signal. The signal s (n) is sent from the control and processing device 11 to the speaker 4 after being converted in a step 210 into an analog signal s(t) via the D/A conversion board 13.

In step 220, a first acoustic pressure $p_1(t)$ and a second acoustic pressure $p_2(t)$ are directly measured at points $x_1$ and $x_2$ by the first and second microphones 9, 10 which output a first electrical signal $r_1(t)$ and a second electrical signal $r_2(t)$ as a function of time, respectively. In a step 230, the control and processing device 11 through the acquisition sound board 14 acquires the first and second electrical signals $r_1(t)$, $r_2(t)$ and converts them through the A/D conversion board 15 into corresponding discretized values $r_1(n)$ and $r_2(n)$, where $\in[1; N]$, $N \in \mathbb{N}$.

The A/D conversion board 15 is synchronized with the D/A conversion board 13, so that the electrical signals $r_1(t)$, $r_2(t)$ are aligned in time, i.e. they are acquired in synchrony with the excitation signal s (t). In other words, the acquisition of electrical signals must begin exactly at the instant in which the excitation signal is emitted.

The number N of discretized values depends on the measurement sampling, i.e. on the temporal resolution of the acquisitions and therefore on the excitation chirp or sweep signal s(n) synthesized in the step 200.

In step 240, the control and processing device 11 calculates the impulse response of the auditory canal 6 according to equation 8, obtaining a first impulse response $\delta_1^{au}(n)$ and a second impulse response $\delta_2^{au}(n)$ from the first and second microphones 9 and 10, respectively:

$$\delta_1^{au}(n) = IFFT\left\{\frac{FFT\{s'(n)\}}{FFT\{r_1(n)\}}\right\}$$ (Eq. 9)

$$\delta_2^{au}(n) = IFFT\left\{\frac{FFT\{s'(n)\}}{FFT\{r_2(n)\}}\right\}$$

The control and processing device 11 processes such impulsive responses $\delta_1^{au}(n)$ and $\delta_2^{au}(n)$, in step 250, to calculate a acoustic pressure impulse response $\delta_p^{au}(n)$ and a velocity impulse response $\delta_v^{au}(n)$ of the air particle at the measuring point $x_0$ according to equations 5 and 6 respectively:

$$\delta_v^{au}(n) = \frac{\delta_1^{au}(n) - \delta_2^{au}(n)}{(\rho \cdot \Delta x_{12})} + \delta_v^{au}(n-1)$$ (Eq. 10)

$$\delta_p^{au}(n) = \frac{\delta_1^{au}(n) + \delta_2^{au}(n)}{2}$$

The apex "au" of the pressure and velocity impulsive responses indicates that they are quantities in arbitrary units [a.u.].

The pressure and velocity impulse responses $\delta_p^{au}(n)$, $\delta_v^{au}(n)$ are then converted by the control and processing device 11 into physical units, multiplying each by a calibration constant $\alpha$ and $\beta$ respectively, in step 260, in order to represent them in the respective physical scales of [Pa] and [m/s]:

$$\delta_p(n)[Pa] = \alpha \frac{[Pa]}{[a.u.]} \cdot \delta_p^{au}(n) [a.u.]$$ (Eq. 11)

$$\delta_v(n)[Pa] = \beta \frac{[m/s]}{[a.u.]} \cdot \delta_v^{au}(n) [a.u.]$$

The calibration constants $\alpha$ and $\beta$ are obtained by means of methods known in literature, see for example Stanzial D., Graffigna C. E., Protocollo di calibrazione in ampiezza e fase per sonde pressione-velocità in un campo di riferimento a onde piane progressive, Associazione Italiana di Acustica, 44° Convegno Nazionale, Pavia, 7-9 giugno 2017 ISBN: 978-88-88942-54-4 wherein the velocity signal is the one reconstructed from the pressure signals of the microphones. In other words, both the signal $p(x_0)$, and the signal $v(x_0)$, which are reconstructed from the signals $p(x_1)$ and $p_2(x_2)$ are calibrated. In further embodiments of this invention, the calibration constants $\alpha$ and $\beta$ are provided by the manufacturers of microphonic probes.

Once the pressure and velocity impulsive responses have been converted into physical units, the Fast Fourier Transform is applied to them in step 270, by the control and processing device 11, to obtain the frequency spectra $\hat{P}^*(\omega_m)$ and $\hat{V}^*(\omega_m)$ of the pressure and velocity impulsive responses:

$$\begin{cases} \hat{V}^*(\omega_m) = FFT\{\delta_v(n)\} \\ \hat{P}^*(\omega_m) = FFT\{\delta_p(n)\} \end{cases}$$ (Eq. 12)

where $\omega_m$ is the discretized frequency with $m \in [1; N/2]$ and the accent ^ indicates that the spectra are complex. The apex * indicates that they are spectra of the impulse responses of measured signals, i.e. the spectra are not calibrated. This is because microphones generally have different responses at different frequencies.

Then, in step 280, a not yet calibrated admittance $\hat{Y}^*(\omega_m)$ is calculated by the control and processing device 11 as the ratio between the cross spectrum $\hat{G}_{pv}(\omega_m)$ of the impulse response spectrum of acoustic pressure and of the impulse response spectrum of acoustic velocity, and the auto spectrum $\hat{G}_{pp}(\omega_m)$ of the impulse response spectrum of the of the acoustic pressure:

$$\hat{Y}^*(\omega_m) = \frac{\hat{G}_{pv}(\omega_m)}{\hat{G}_{pp}(\omega_m)} = \frac{\hat{V}^*(\omega_m) \cdot \hat{P}^*(\omega_m)}{\hat{P}^*(\omega_m) \cdot \hat{P}^*(\omega_m)}$$ (Eq. 13)

Finally, in step 290, a measurement of the calibrated admittance of the auditory canal 6 is obtained by means of the control and processing device 11 as:

$$\hat{Y}(\omega_m) = \Gamma(\omega_m) \cdot \hat{Y}^*(\omega_m) \qquad \text{(Eq. 14)}$$

where $\Gamma(\omega_m)$ is a frequency calibration curve obtained according to an amplitude and phase calibration protocol developed by the inventors for pressure-velocity probes in a plane wave reference field (Stanzial D., Graffigna C. E., Funzione di calibrazione in ampiezza efase per sonde pressione-velocità ottenuta in campi di riferimento reattivi, Associazione Italiana di Acustica, 45° Convegno Nazionale, Aosta, 20-22 giugno 2018 ISBN: 978-88-88942-56-8), wherein the velocity signal is the one reconstructed from the pressure signals of the microphonic probes.

The calibration curve $\Gamma(\omega_m)$ takes in account of different responses of the microphonic probes as the frequency varies. In further embodiments of the present invention, calibration functions $\Gamma(\omega_m)$ are provided by the manufacturers of the microphonic probes.

The admittance spectrum $\hat{Y}(\omega_m)$, magnitude and phase, is optionally displayed at the output on a screen 16 in step 295.

From the acoustic admittance $\hat{Y}(\omega_m)$ all the classical tympanometric parameters can be evaluated, such as for example the tympanic rigidity, the volume of the auditory canal. In other words, the parameters used for the audiometric clinical investigation are calculated from the resonance curve obtained through the admittance measured in the auditory canal.

The separation of the volume of air inside the auditory canal from that inside the probe, the absorption of energy by the eardrum and other parameters useful for diagnostic purposes are obtained from the analysis of the shape of the resonance curve of the acoustic admittance.

In the embodiments of the method according to the invention in which the microphonic probe 8 includes a plurality of microphonic probes greater than two, the steps described above are performed for each combination of pair of microphones having distances $\Delta x_{ij}$ that are different from each other. Subsequently, the frequency admittance curve would be recomposed for each processed frequency segment.

Since it is very important that the coupling of the impedance probe 2 with the auditory canal 6 is proper, i.e. that the volume $V_{probe}$ of the air of the impedance probe 2 and the volume $V_{canal}$ of the air inside the auditory canal 6 form an overall volume $V_{overall}$ of air at atmospheric pressure, optionally a preliminary procedure is performed to identify the right coupling of the probe to the auditory canal. This preliminary procedure is based on the identification of the resonance of the admittance. Once the resonance has been identified, a more accurate admittance measurement is carried out to obtain the clinical-audiometric parameters while maintaining the coupling of the impedance probe with the auditory canal for which the resonance occurs.

This preliminary procedure includes carrying out the method wherein an impedance probe (1) is coupled, for example from an operator, with the auditory canal (6) of a patient in a first coupling configuration (Q1) and wherein a fast sweep signal $s^{fast}(t)$, with $T_{sweep}^{fast}$ less than one second, optionally equal to about half a second. The above-described steps of the method are performed to obtain a first calibrated admittance $\hat{Y}_1(\omega_m)$ of the auditory canal 6.

It is checked whether a resonance condition in the admittance is satisfied, that is if the peak of the admittance module corresponds with the zero-crossing of its phase.

If a resonance condition occurs, the first coupling configuration (Q1) corresponds to the right coupling of the probe with the auditory canal and the said procedure ends.

The method is then executed keeping the first coupling configuration (Q1) and sending a slow sweep signal s(t), i.e., with $T_{sweep}$ less than 10 seconds and greater or equal to 1 second for measuring the calibrated $\hat{Y}(\omega_m)$ from which obtaining the audiometric parameters of the auditory canal.

If a resonance condition does not occur, then the method is iterated in a second coupling configuration (Q2) that is different in respect to the previous one (Q1), for example the operator changes the mutual and placement of probe and auditory canal, and with the fast sweep signal $s^{fast}(t)$ obtaining a second calibrated admittance $\hat{Y}_2(\omega_m)$ and the checking is iterated.

In other words, a resonance in the admittance spectrum implies that the impedance probe is positioned correctly in respect to the ear and a more accurate measurement can be performed for determining the admittance.

In a preferred embodiment of the method, if the resonance condition is verified, the control and processing device 11 alerts an operator, for example by emitting a sound signal or by sending a signal on a screen, so that the configuration of coupling for which resonance occurs can be kept while performing the final measurement. The preferred embodiments of this invention have been described, but it must be understood that those skilled in the art can make other variations and changes, without so departing from the scope of protection thereof, as defined by the attached claims.

The invention claimed is:

1. A method for determining the admittance of an auditory canal for clinical-audiometric investigations, the method comprising at least one or more iterations of a procedure, in which each iteration is associated with a respective coupling configuration between an impedance probe and the auditory canal, in which said procedure includes the following steps:

A. coupling the calibrated sealed impedance probe having a known air volume $V_{probe}$, through a first end thereof, with the auditory canal so that:
      the air volume $V_{probe}$ sealed inside the impedance probe and the air volume $V_{canal}$ inside the auditory canal form an overall air volume $V_{overall}$, and
      a longitudinal axis of the impedance probe is substantially coincident to a longitudinal axis of the auditory canal;

B. sending a broadband exciting sound signal s(t) to the auditory canal through a speaker of the impedance probe, such speaker being located at a second end of the impedance probe opposed to the first end;

C. directly detecting an acoustic pressure $p_1(t)$, $p_2(t)$ back from the auditory canal in at least two points $x_1$ and $x_2$, respectively, located along the longitudinal axis of the impedance probe at distance $\Delta x_{12}$ between them, by means of a microphone array that is included in the impendence probe and outputs electric signals $r_1(t)$ and $r_2(t)$;

D. acquiring and discretizing the output electric signals $r_1(t)$ and $r_2(t)$ from the microphone array, obtaining discretized signals $r_1(n)$ and $r_2(n)$ respectively, with $n \in [1; N]$, $N \in \mathbb{N}$;

E. calculating a first impulse response $\delta_1^{au}(n)$ and a second impulse response $\delta_2^{au}(n)$ by the following equations:

$$\delta_1^{au}(n) = IFFT\left\{\frac{FFT\{s'(t)\}}{FFT\{r_1(t)\}}\right\}$$

$$\delta_2^{au}(n) = IFFT\left\{\frac{FFT\{s'(t)\}}{FFT\{r_2(t)\}}\right\}$$

where s'(t) is the time reversed broadband sound signal s(t), FFT is a Fast Fourier Transform and IFFT is an inverse FFT;

F. calculating an impulse response $\delta_p^{au}(n)$ of the acoustic pressures $p_1(t)$ and $p_2(t)$ and an impulse response $\delta_v^{au}(n)$ of velocity of an air particle at measurement point $x_0$ along the longitudinal axis of the impedance probe:

$$\delta_v^{au}(n) = \frac{\delta_1^{au}(n) - \delta_2^{au}(n)}{(\rho \cdot \Delta x_{12})} + \delta_v^{au}(n-1)$$

$$\delta_p^{au}(n) = \frac{\delta_1^{au}(n) + \delta_2^{au}(n)}{2}$$

such a measurement point $x_0$ being a centre point between points $x_1$ and $x_2$;

G. converting the impulse responses $\delta_p^{au}(n)$, $\delta_v^{au}(n)$ of pressure and velocity to pressure and velocity physical units by multiplying each one by a calibration constant $\alpha$ and $\beta$ known a priori, respectively, as follows:

$$\delta_p(n)[Pascal] = \alpha \cdot \delta_p^{au}(n)$$

$$\delta_v(n)[Pascal\ meter/second] = \beta \cdot \delta_v^{au}(n)$$

H. calculating frequency spectra $\hat{P}^*(\omega_m)$, $\hat{V}^*(\omega_m)$ of the impulse responses of pressure and velocity respectively, through Fast Fourier Transform, as follows:

$$\begin{cases} \hat{V}^*(\omega_m) = FFT\{\delta_v(n)\} \\ \hat{P}^*(\omega_m) = FFT\{\delta_p(n)\} \end{cases}$$

where $\omega_m$ is a discretized frequency with me [1; N/2];

I. calculating an admittance $\hat{Y}^*(\omega_m)$ as a ratio between a cross spectrum $\hat{G}_{pv}(\omega_m)$ of the spectrum of the acoustic pressure impulse response and of the spectrum of the acoustic velocity impulse response, and an auto spectrum $\hat{G}_{pp}(\omega_m)$ of the spectrum of the acoustic pressure impulse response:

$$\hat{Y}^*(\omega_m) = \frac{\hat{G}_{pv}(\omega_m)}{\hat{G}_{pp}(\omega_m)} = \frac{\hat{V}^*(\omega_m) \cdot \hat{P}^*(\omega_m)}{\hat{P}^*(\omega_m) \cdot \hat{P}^*(\omega_m)}$$

L. obtaining a calibrated frequency spectrum $\hat{Y}(\omega_m)$ of the admittance through a calibration function $\Gamma(\omega_m)$ known a priori, according to the equation:

$$\hat{Y}(\omega_m) = \Gamma(\omega_m) \cdot \hat{Y}^*(\omega_m),$$

said steps D to L being performed by a control and processing device.

2. The method according to claim 1, wherein the exciting sound signal s(t) is a sweep signal, varying from a minimum frequency $F_{min}$ greater than 100 Hz to a maximum frequency $F_{max}$ less then 5000 Hz over a time $T_{sweep}$ less than 10 seconds.

3. The method according to claim 2, wherein the distance $\Delta x_{12}$ is equal to 12 mm.

4. The method according to claim 2, wherein step B comprises the substeps:
B.1 synthesizing a digital sweep signal s(n) by a signal generator,
B.2 converting the digital sweep signal s(n) into a broadband exciting sound signal s(t) to be input to the speaEker through a D/A converter.

5. The method according to claim 4, wherein step D is implemented through an A/D converter synchronized with the D/A converter.

6. The method according to claim 1, wherein the calibrated frequency spectrum $\hat{Y}(\omega_m)$ of the admittance is further input to a display to be displayed.

7. The method according to claim 1, wherein the impedance probe and the auditory canal are coupled into a first coupling configuration, the exciting sound signal s(t) is a fast sweep signal $s^{fast}(t)$ varying in frequency over a time $T_{sweep}^{fast}$ less than one second, to obtain a first calibrated admittance $\hat{Y}_1(\omega_m)$ and said procedure comprises further the additional step:
M. checking whether a resonance condition in the calibrated admittance $\hat{Y}_1(\omega_m)$ is satisfied, thereby a peak of the module of the first calibrated admittance $\hat{Y}_1(\omega_m)$ corresponds to zero-crossing of its phase, and wherein:
if a resonance condition does not occur, another iteration of said procedure comprising steps A to M is implemented, wherein the impedance probe and the auditory canal are coupled in another coupling configuration that is different from the previous coupling configuration and the exciting sound signal s(t) is the fast sweep signal $s^{fast}(t)$;
if a resonance condition occurs, steps B to L of such procedure are implemented, wherein the coupling configuration is the one for which the resonance condition occurs and the exciting sound signal s(t) is a slow sweep signal varying in frequency over a time $T_{sweep}$, wherein $T_{sweep}$ is greater than the time $T_{sweep}^{fast}$ of the fast sweep signal $s^{fast}(t)$, and said one or more iterations of said procedure end.

8. A clinical-audiometric investigation method comprising a method for determining the admittance of an auditory canal comprising at least one or more iterations of a procedure, in which each iteration is associated with a respective coupling configuration between a impedance probe and the auditory canal, in which said procedure includes the following steps:
A. coupling the calibrated sealed impedance probe having a known air volume $V_{probe}$, through a first end thereof, with the auditory canal so that:
the air volume $V_{probe}$ sealed inside the impedance probe and the air volume $V_{canal}$ inside the auditory canal form an overall air volume $V_{overall}$, and
a longitudinal axis of the impedance probe is substantially coincident to a longitudinal axis of the auditory canal;
B. sending a broadband exciting sound signal s(t) to the auditory canal through a speaker of the impedance probe, such speaker being located at a second end of the impedance probe opposed to the first end;
C. directly detecting an acoustic pressure $p_1(t)$, $p_2(t)$ back from the auditory canal in at least two points $x_1$ and $x_2$, respectively, located along the longitudinal axis of the impedance probe at distance $\Delta x_{12}$ between them, by means of a microphone array that is included in the impendence probe and outputs electric signals $r_1(t)$ and $r_2(t)$;

D. acquiring and discretizing the output electric signals $r_1(t)$ and $r_2(t)$ from the microphone array, obtaining discretized signals $r_1(n)$ and $r_2(n)$ respectively, with $n \in [1; N]$, $N \in \mathbb{N}$;

E. calculating a first impulse response $\delta_1^{au}(n)$ and a second impulse response $\delta_2^{au}(n)$ by the following equations:

$$\delta_1^{au}(n) = IFFT\left\{\frac{FFT\{s'(t)\}}{FFT\{r_1(t)\}}\right\}$$

$$\delta_2^{au}(n) = IFFT\left\{\frac{FFT\{s'(t)\}}{FFT\{r_2(t)\}}\right\}$$

where $s'(t)$ is the time reversed broadband sound signal $s(t)$, FFT is a Fast Fourier Transform and IFFT is an inverse FFT;

F. calculating an impulse response $\delta_p^{au}(n)$ of the acoustic pressures $p_1(t)$ and $p_2(t)$ and an impulse response $\delta_v^{au}(n)$ of velocity of an air particle at measurement point $x_0$ along the longitudinal axis of the impedance probe:

$$\delta_v^{au}(n) = \frac{\delta_1^{au}(n) - \delta_2^{au}(n)}{(\rho \cdot \Delta x_{12})} + \delta_v^{au}(n-1)$$

$$\delta_p^{au}(n) = \frac{\delta_1^{au}(n) + \delta_2^{au}(n)}{2}$$

such a measurement point $x_0$ being a centre point between points $x_1$ and $x_2$;

G. converting the impulse responses $\delta_p^{au}(n)$, $\delta_v^{au}(n)$ of pressure and velocity to pressure and velocity physical units by multiplying each one by a calibration constant $\alpha$ and $\beta$ known a priori, respectively, as follows:

$\delta_p(n)[\text{Pascal}] = \alpha \cdot \delta_p^{au}(n)$ $\delta_v(n)[\text{Pascal meter/second}] = \beta \cdot \delta_v^{au}(n)$ H. calculating frequency spectra $\hat{P}^*(\omega_m)$, $\hat{V}^*(\omega_m)$ of the impulse responses of pressure and velocity respectively, through Fast Fourier Transform, as follows:

$$\begin{cases} \hat{V}^*(\omega_m) = FFT\{\delta_v(n)\} \\ \hat{P}^*(\omega_m) = FFT\{\delta_p(n)\} \end{cases}$$

where $\omega_m$ is a discretized frequency with $m \in [1; N/2]$;

I. calculating an admittance $\hat{Y}^*(\omega_m)$ as a ratio between a cross spectrum $\hat{G}_{pv}(\omega_m)$ of the spectrum of the acoustic pressure impulse response and of the spectrum of the acoustic velocity impulse response, and an auto spectrum $\hat{G}_{pp}(\omega_m)$ of the spectrum of the acoustic pressure impulse response:

$$\hat{Y}^*(\omega_m) = \frac{\hat{G}_{pv}(\omega_m)}{\hat{G}_{pp}(\omega_m)} = \frac{\hat{V}^*(\omega_m) \cdot \hat{P}^*(\omega_m)}{\hat{P}^*(\omega_m) \cdot \hat{P}^*(\omega_m)}$$

L. obtaining a calibrated frequency spectrum $(\omega_m)$ of the admittance through a calibration function $\Gamma(\omega_m)$ known a priori, according to the equation:

$\hat{Y}(\omega_m) = \Gamma(\omega_m) \cdot \hat{Y}^*(\omega_m)$ said steps D to L being performed by a control and processing device, wherein the investigation is implemented in the coupling configuration of the last one or more iterations and wherein the exciting sound signal $s(t)$ varies in frequency over a time grater or equal to 1 second.

9. An apparatus configured to executed a method for determining the admittance of an auditory canal for clinical-audiometric investigations comprising at least one or more iterations of a procedure, in which each iteration is associated with a respective coupling configuration between an impedance probe and the auditory canal, in which said procedure includes the following steps:

A. coupling the calibrated sealed impedance probe having a known air volume $V_{probe}$, through a first end thereof, with the auditory canal so that:
the air volume $V_{probe}$ sealed inside the impedance probe and the air volume $V_{canal}$ inside the auditory canal form an overall air volume $V_{overall}$, and
a longitudinal axis of the impedance probe is substantially coincident to a longitudinal axis of the auditory canal;

B. sending a broadband exciting sound signal $s(t)$ to the auditory canal through a speaker of the impedance probe, such speaker being located at a second end of the impedance probe opposed to the first end;

C. directly detecting an acoustic pressure $p_1(t)$, $p_2(t)$ back from the auditory canal in at least two points $x_1$ and $x_2$, respectively, located along the longitudinal axis of the impedance probe at distance $\Delta x_{12}$ between them, by means of a microphone array that is included in the impendence probe and outputs electric signals $r_1(t)$ and $r_2(t)$;

D. acquiring and discretizing the output electric signals $r_1(t)$ and $r_2(t)$ from the microphone array, obtaining discretized signals $r_1(n)$ and $r_2(n)$ respectively, with $n \in [1; N]$, $N \in \mathbb{N}$;

E. calculating a first impulse response $\delta_1^{au}(n)$ and a second impulse response $\delta_2^{au}(n)$ by the following equations:

$$\delta_1^{au}(n) = IFFT\left\{\frac{FFT\{s'(t)\}}{FFT\{r_1(t)\}}\right\}$$

$$\delta_2^{au}(n) = IFFT\left\{\frac{FFT\{s'(t)\}}{FFT\{r_2(t)\}}\right\}$$

where $s'(t)$ is the time reversed broadband sound signal $s(t)$, FFT is a Fast Fourier Transform and IFFT is an inverse FFT;

F. calculating an impulse response $\delta_p^{au}(n)$ of the acoustic pressures $p_1(t)$ and $p_2(t)$ and an impulse response $\delta_v^{au}(n)$ of velocity of an air particle at measurement point $x_0$ along the longitudinal axis of the impedance probe:

$$\delta_v^{au}(n) = \frac{\delta_1^{au}(n) - \delta_2^{au}(n)}{(\rho \cdot \Delta x_{12})} + \delta_v^{au}(n-1)$$

-continued $$\delta_p^{au}(n) = \frac{\delta_1^{au}(n) + \delta_2^{au}(n)}{2}$$

such a measurement point $x_0$ being a centre point between points $x_1$ and $x_2$;

G. converting the impulse responses $\delta_p^{au}(n)$, $\delta_v^{au}(n)$ of pressure and velocity to pressure and velocity physical units by multiplying each one by a calibration constant $\alpha$ and $\beta$ known a priori, respectively, as follows:

$$\delta_p(n)[\text{Pascal}] = \alpha \cdot \delta_p^{au}(n)$$

$$\delta_v(n)[\text{Pascal meter/second}] = \beta \cdot \delta_v^{au}(n)$$

H. calculating frequency spectra $\hat{P}^*(\omega_m)$, $\hat{V}^*(\omega_m)$ of the impulse responses of pressure and velocity respectively, through Fast Fourier Transform, as follows:

$$\begin{cases} \hat{V}^*(\omega_m) = FFT\{\delta_v(n)\} \\ \hat{P}^*(\omega_m) = FFT\{\delta_p(n)\} \end{cases}$$

where $\omega_m$ is a discretized frequency with $m \in [1; N/2]$;

I. calculating an admittance $\hat{Y}^*(\omega_m)$ as a ratio between a cross spectrum $\hat{G}_{pv}(\omega_m)$ of the spectrum of the acoustic pressure impulse response and of the spectrum of the acoustic velocity impulse response, and an auto spectrum $\hat{G}_{pp}(\omega_m)$ of the spectrum of the acoustic pressure impulse response:

$$\hat{Y}^*(\omega_m) = \frac{\hat{G}_{pv}(\omega_m)}{\hat{G}_{pp}(\omega_m)} = \frac{\hat{V}^*(\omega_m) \cdot \hat{P}^*(\omega_m)}{\hat{P}^*(\omega_m) \cdot \hat{P}^*(\omega_m)}$$

L. obtaining a calibrated frequency spectrum $\hat{Y}(\omega_m)$ of the admittance through a calibration function $\Gamma(\omega_m)$ known a priori, according to the equation:

$$\hat{Y}(\omega_m) = \Gamma(\omega_m) \cdot \hat{Y}^*(\omega_m),$$

said apparatus including:
an impedance probe configured to be coupled with an auditory canal having
  a body with a first end configured to be coupled to the auditory canal,
  a speaker located close to a second end of the body, that is opposed to the first end, configured to emit an exciting sound signal, the body being sealed and containing inside an air volume $V_{probe}$ at atmospheric pressure,
  a microphone array housed inside the body and configured to detect signals back from the auditory canal, comprising at least a first microphone and at least a second microphone placed between them at a distance $\Delta x_{12}$ that depends on the frequencies of the exciting sound signal s(t), each microphone being configured to directly detect a return sound pressure p(x, t) as a function of time t and to output an electrical signal r (x, t);
a control and processing device configured to control and process input and output signals of the impedance probe and to implement step B to L, having:
  a generation unit configured to generate a digital signal s(n) and send it to the speaker through a D/A conversion board that is removably coupled to the speaker, and
  an acquisition sound board configured to acquiring output signal from microphone array, through an A/D conversion board that is removably coupled to the microphone array,
  the impedance probe and the control and processing device being removably coupled among them.

10. The apparatus according to claim 9, wherein the apparatus is configured to execute a first iteration of said procedure associated with a first coupling configuration between the impedance probe and the auditory canal and said exciting sound signal s(t) is a fast sweep signal $s^{fast}(t)$ varying in frequency over a time $T_{sweep}^{fast}$ less than one second to obtain a first calibrated admittance $\hat{Y}_1(\omega_m)$ and the control and processing device is further configured to execute the following step M for each one of said one or more iteration:

M. checking whether a resonance condition in the calibrated admittance $\hat{Y}_1(\omega_m)$ is satisfied, thereby a peak of the module of the first calibrated admittance $\hat{Y}_1(\omega_m)$ corresponds to zero-crossing of its phase, and wherein:
  if a resonance condition does not occur, another iteration of said procedure comprising steps A to M is implemented, wherein the impedance probe and the auditory canal are coupled in another coupling configuration that is different from the previous coupling configuration and the exciting sound signal s(t) is the fast sweep signal $s^{fast}(t)$;
  if a resonance condition occurs, steps B to L of such procedure are implemented, wherein the coupling configuration is the one for which the resonance condition occurs and the exciting sound signal s(t) is a slow sweep signal varying in frequency over a time $T_{sweep}$, wherein $T_{sweep}$ is greater than the time $T_{sweep}^{fast}$ of the fast sweep signal $s^{fast}(t)$, and said one or more iterations of said procedure end.

11. The apparatus according claim 9, wherein the body is hollow cylindrical shaped.

12. The apparatus according claim 9, configured to input broadband exciting sound signal s(t) in a frequency range between 100 Hz to 5000 Hz and wherein the distance $\Delta x_{12}$ is equal to 12 mm.

13. The apparatus according to claim 9, wherein the second end is provided with an adapter configured to couple with the auditory canal.

14. The apparatus according to claim 13, wherein the adapter is truncated cone shaped.

15. The method according to claim 1, wherein the calibration constant $\alpha$ and $\beta$, and the calibration function $\Gamma(\omega_m)$ are provided by manufacturer of microphones.

16. The method according to claim 2, wherein the sweep signal is a linear or logarithmic sinusoidal signal.

17. The method according to claim 2, wherein the time $T_{sweep}$ is equal to 2 seconds.

18. The method according to claim 2, wherein the time $T_{sweep}$ is equal to 1 seconds.

19. The apparatus according to claim 13, wherein said adapter is removable.

20. The apparatus according to claim 13, wherein said adapter is made of rubber latex.

21. The method of claim 7, further comprising: if the resonance condition occurs at step M, generating an alert, wherein the alert comprises at least one of emitting a sound signal alert and an on-screen signal.

22. The Apparatus of claim 10, wherein the control and processing device apparatus is further configured to, if the resonance condition occurs at step M, generate an alert, wherein the alert comprises at least one of emitting a sound signal alert and an on-screen signal.

\* \* \* \* \*